United States Patent
Lu et al.

(10) Patent No.: US 11,124,506 B2
(45) Date of Patent: Sep. 21, 2021

(54) SALTS AND CRYSTAL FORMS OF DIAZA-BENZOFLUORANTHRENE COMPOUNDS

(71) Applicant: HARBIN PHARMACEUTICAL GROUP CO., LTD. GENERAL PHARMACEUTICAL FACTORY, Heilongjiang (CN)

(72) Inventors: Qingqing Lu, Shanghai (CN); Shenyi Shi, Shanghai (CN); Tiezhong Bai, Heilongjiang (CN); Shujie Yuan, Heilongjiang (CN); Zhengwu Li, Heilongjiang (CN); Qiaofen Hu, Heilongjiang (CN); Yijie Cao, Heilongjiang (CN); Jing Gao, Heilongjiang (CN); Hui Ding, Heilongjiang (CN); Jinhua Li, Heilongjiang (CN); Guanghai Xu, Shanghai (CN); Zheng Wang, Shanghai (CN); Xin Jin, Heilongjiang (CN)

(73) Assignee: HARBIN PHARMACEUTICAL GROUP CO., LTD. GENERAL PHARMACEUTICAL FACTORY, Harbin (CN)

( * ) Notice: Subject to any disclaimer, the term of this patent is extended or adjusted under 35 U.S.C. 154(b) by 0 days.

(21) Appl. No.: 16/322,937

(22) PCT Filed: Aug. 3, 2017

(86) PCT No.: PCT/CN2017/095762
§ 371 (c)(1),
(2) Date: Feb. 2, 2019

(87) PCT Pub. No.: WO2018/024225
PCT Pub. Date: Feb. 8, 2018

(65) Prior Publication Data
US 2019/0169183 A1 Jun. 6, 2019

(30) Foreign Application Priority Data
Aug. 4, 2016 (CN) .......................... 201610633622.7

(51) Int. Cl.
| | | |
|---|---|---|
| *C07D 461/00* | (2006.01) | |
| *A61P 9/10* | (2006.01) | |
| *A61P 25/08* | (2006.01) | |
| *C07C 59/265* | (2006.01) | |

(52) U.S. Cl.
CPC .............. *C07D 461/00* (2013.01); *A61P 9/10* (2018.01); *A61P 25/08* (2018.01); *C07C 59/265* (2013.01); *C07B 2200/13* (2013.01)

(58) Field of Classification Search
CPC .................................. C07D 461/00; A61P 9/10
See application file for complete search history.

(56) References Cited

FOREIGN PATENT DOCUMENTS

WO    2016/124129 A1    8/2016

OTHER PUBLICATIONS

Berge et al., "Pharmaceutical Salts" Journal of Pharmaceutical Sciences; 1977; vol. 66, No. 1; pp. 1-19.*
International Search Report of PCT Patent Application No. PCT/CN2017/095762 dated Oct. 26, 2017.

* cited by examiner

*Primary Examiner* — Rebecca L Anderson

(57) ABSTRACT

The present invention discloses to a hydrochloride salt, a citrate salt, a phosphate salt or a sulfate salt of compound 1, the crystal forms of the aforementioned salts, and a preparation method thereof. The present invention also relates their use in the preparation of a medicament for the treatment of cerebral apoplexy or epilepsy.

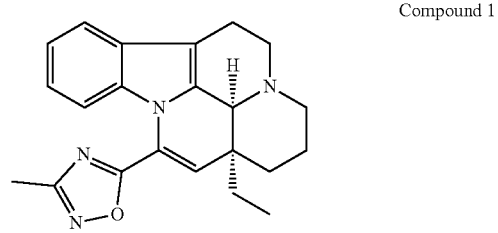

Compound 1

37 Claims, No Drawings

SALTS AND CRYSTAL FORMS OF DIAZA-BENZOFLUORANTHRENE COMPOUNDS

FIELD OF THE INVENTION

The present invention relates to a hydrochloride salt, a citrate salt, a phosphate salt or a sulfate salt of compound 1, the crystal forms of the aforementioned salts, and a preparation method thereof. The present invention also relates to their use in the preparation of a medicament for the treatment of cerebral apoplexy or epilepsy.

BACKGROUND OF THE INVENTION

According to the research of the World Health Organization (WHO), cerebral apoplexy has become the second leading cause of death, following ischemic heart disease; cerebral apoplexy is also very likely to lead to deformity and disability. It seriously affects the quality of life of patients and their family. Therefore, it is necessary to find a way to improve the health conditions of patients suffering from apoplexy and to restore their body function and ability to work, so that they can have a better quality of life and a good prognosis. This is beneficial to reduce the burden of not only individuals but also the whole society.

Vinpocetine, which is represented by the formula B-I, is an indole alkaloid extracted from the lesser periwinkle plant. Vinpocetine is highly fat-soluble and can easily pass through the blood-brain barrier, so it is present in high concentration in brain tissues and have good efficacy. Vinpocetine is developed by Gedeon Richter Co., a Hungarian company, in 1978. It has a history of over 30 years in Europe. It is mainly used to relieve the symptoms caused by cerebral infarction sequelae, cerebral hemorrhage sequelae, and cerebral atherosclerosis, among others. Ever since vinpocetine first came into the market, it is regarded as a routine medicine to treat cardiovascular and cerebrovascular diseases. Recently, it is found that vinpocetine can improve age-related memory impairment and the mental activities of healthy people. In addition, it is found that vinpocetine can also act to treat confusion, attention-deficit disorder, irritability, visual and auditory disorders, and emotional fluctuation, among others. In addition, according to clinical trial data, for over 67% of seizures, the seizure occurrence rate is significantly reduced or there had been no incidence at all. It has a significant therapeutic effect on generalized tonic-clonic seizures.

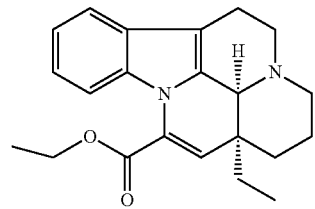

(B-I)

The incidence rate and disability rate of cerebral apoplexy are very high in China, which has become a heavy burden for the Chinese medical system. Vinpocetine is widely used for treating cerebral apoplexy and other related diseases in China; it is the main treatment method to improve the prognosis of cerebral apoplexy. However, the therapeutic effect of vinpocetine is still debatable, and the bioavailability of vinpocetine tablets is quite low.

Epilepsy is a chronic recurrent transient brain dysfunction syndrome and is characterized by an abnormal discharge of neurons in the brain, which leads to a risk of recurrent seizures. Epilepsy is a common nervous system disease. Its prevalence is second only to cerebral apoplexy. The number of epilepsy patients in China is large, and the majority of patients are young adults and children under the age of 20. Its disability rate and mortality rate are also high, which has become a problem of concern for the whole society. Vinpocetine has various degrees of efficacy for over 67% of epilepsy patients, especially for generalized tonic-clonic seizures.

SUMMARY OF THE INVENTION

The present invention provides a hydrochloride salt, a citrate salt, a phosphate salt or a sulfate salt of compound 1.

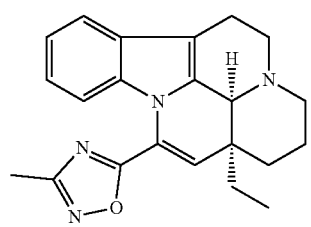

Compound 1

In some embodiments of the present applicant, the hydrochloride salt, the citrate salt, the phosphate salt or the sulfate salt of the aforementioned compound 1 is selected from:

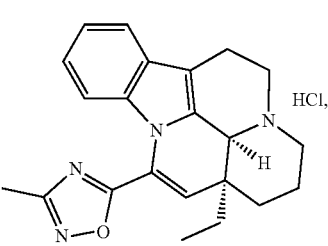

(I)

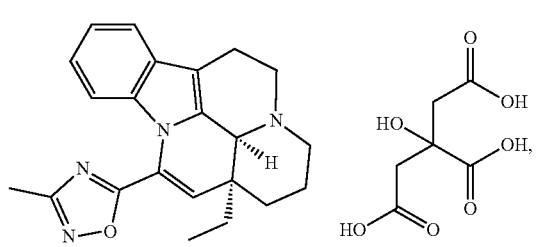

(II)

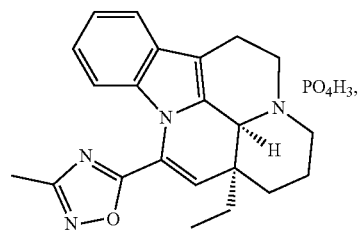

(III)

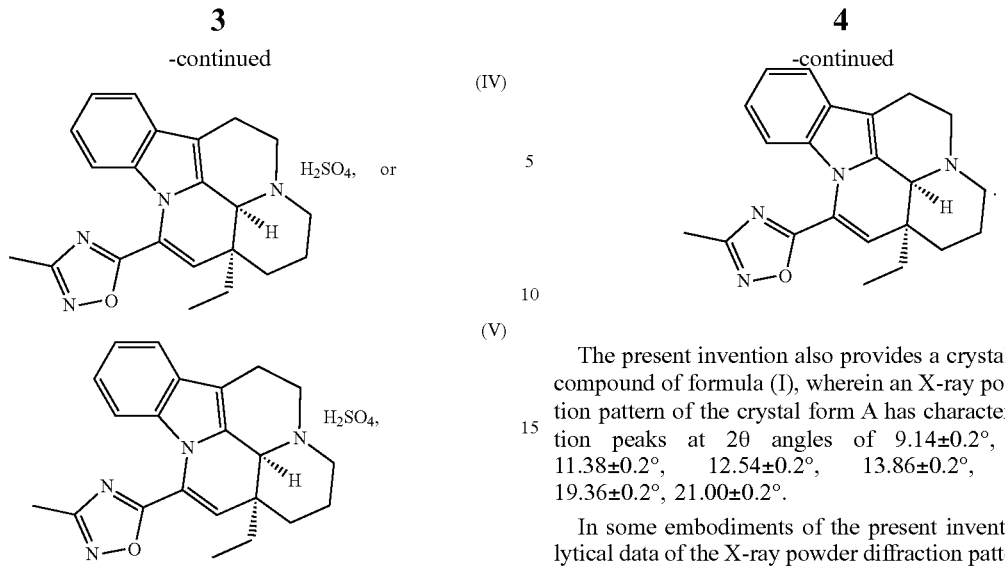

The present invention also provides a crystal form A of a compound of formula (I), wherein an X-ray powder diffraction pattern of the crystal form A has characteristic diffraction peaks at 2θ angles of 9.14±0.2°, 10.43±0.2°, 11.38±0.2°, 12.54±0.2°, 13.86±0.2°, 19.04±0.2°, 19.36±0.2°, 21.00±0.2°.

In some embodiments of the present invention, the analytical data of the X-ray powder diffraction pattern of crystal form A of the compound of formula (I) is shown in Table-1.

TABLE 1 analytical data of X-ray powder diffraction pattern of crystal form A of compound of formula (I)

| NO. | 2-Theta | d(A) | BG | Height | I % | Area | I % | FWHM |
|---|---|---|---|---|---|---|---|---|
| 1 | 6.939 | 12.7281 | 194 | 303 | 10.1 | 2387 | 9.8 | 0.132 |
| 2 | 9.145 | 9.6619 | 159 | 3007 | 100 | 24372 | 100 | 0.136 |
| 3 | 10.429 | 8.4755 | 166 | 1735 | 57.7 | 21585 | 88.6 | 0.209 |
| 4 | 11.375 | 7.7723 | 163 | 1175 | 39.1 | 8803 | 36.1 | 0.126 |
| 5 | 12.541 | 7.0524 | 143 | 702 | 23.3 | 5792 | 23.8 | 0.138 |
| 6 | 13.86 | 6.3841 | 140 | 1851 | 61.6 | 15060 | 61.8 | 0.136 |
| 7 | 14.667 | 6.0344 | 156 | 434 | 14.4 | 2968 | 12.2 | 0.115 |
| 8 | 17.091 | 5.1838 | 117 | 347 | 11.5 | 5241 | 21.5 | 0.253 |
| 9 | 18.121 | 4.8914 | 119 | 356 | 11.8 | 2772 | 11.4 | 0.131 |
| 10 | 19.044 | 4.6564 | 114 | 448 | 14.9 | 5014 | 20.6 | 0.188 |
| 11 | 19.364 | 4.58 | 111 | 672 | 22.3 | 7584 | 31.1 | 0.189 |
| 12 | 21 | 4.2269 | 118 | 791 | 26.3 | 16129 | 66.2 | 0.342 |
| 13 | 22.89 | 3.882 | 112 | 228 | 7.6 | 4152 | 17 | 0.305 |
| 14 | 23.857 | 3.7267 | 110 | 231 | 7.7 | 2565 | 10.5 | 0.186 |
| 15 | 25.041 | 3.5532 | 106 | 424 | 14.1 | 5190 | 21.3 | 0.205 |
| 16 | 25.931 | 3.4331 | 105 | 241 | 8 | 1966 | 8.1 | 0.137 |
| 17 | 27.431 | 3.2488 | 102 | 112 | 3.7 | 1649 | 6.8 | 0.247 |
| 18 | 27.822 | 3.204 | 96 | 242 | 8 | 3602 | 14.8 | 0.249 |
| 19 | 28.611 | 3.1173 | 94 | 207 | 6.9 | 1940 | 8 | 0.157 |
| 20 | 29.849 | 2.9908 | 101 | 108 | 3.6 | 1707 | 7 | 0.265 |
| 21 | 31.86 | 2.8065 | 102 | 129 | 4.3 | 1503 | 6.2 | 0.195 |

The present invention also provides a crystal form B of the compound of formula (I), wherein an X-ray powder diffraction pattern of the crystal form B has characteristic diffraction peaks at 2θ angles of 9.17±0.2°, 11.75±0.2°, 12.16±0.2°, 12.67±0.2°, 15.14±0.2°, 17.81±0.2°, 20.54±0.2°, 22.34±0.2°.

In some embodiments of the present invention, the analytical data of the X-ray powder diffraction pattern of crystal form B of the compound of formula (I) described above is shown in Table-2.

TABLE 2 analytical data of X-ray powder diffraction pattern of crystal form B of compound of formula (I)

| NO. | 2-Theta | d(A) | BG | Height | I % | Area | I % | FWHM |
|---|---|---|---|---|---|---|---|---|
| 1 | 9.169 | 9.6372 | 152 | 2286 | 100 | 14460 | 100 | 0.106 |
| 2 | 11.75 | 7.5254 | 129 | 373 | 16.3 | 2694 | 18.6 | 0.121 |
| 3 | 12.159 | 7.273 | 124 | 387 | 16.9 | 3007 | 20.8 | 0.13 |
| 4 | 12.671 | 6.9802 | 123 | 162 | 7.1 | 1021 | 7.1 | 0.106 |

TABLE 2-continued analytical data of X-ray powder diffraction pattern
of crystal form B of compound of formula (I)

| NO. | 2-Theta | d(A) | BG | Height | I % | Area | I % | FWHM |
|---|---|---|---|---|---|---|---|---|
| 5 | 15.135 | 5.8492 | 111 | 147 | 6.4 | 1564 | 10.8 | 0.178 |
| 6 | 17.604 | 5.0339 | 104 | 119 | 5.2 | 1433 | 9.9 | 0.202 |
| 7 | 17.808 | 4.9766 | 104 | 324 | 14.2 | 3418 | 23.6 | 0.177 |
| 8 | 18.786 | 4.7196 | 100 | 81 | 3.5 | 1440 | 10 | 0.298 |
| 9 | 20.542 | 4.32 | 92 | 206 | 9 | 2207 | 15.3 | 0.18 |
| 10 | 22.336 | 3.9769 | 94 | 172 | 7.5 | 1576 | 10.9 | 0.154 |
| 11 | 23.107 | 3.8459 | 95 | 115 | 5 | 854 | 5.9 | 0.124 |
| 12 | 24.546 | 3.6236 | 86 | 93 | 4.1 | 1096 | 7.6 | 0.198 |

The present invention also provides a crystal form C of the compound of formula (II), wherein the X-ray powder diffraction pattern of the crystal form C has characteristic diffraction peaks at 2θ angles of 14.04±0.2°, 16.28±0.2°, 16.70±0.2°, 17.73±0.2°, 18.18±0.2°, 20.29±0.2°, 23.40±0.2°, 25.95±0.2°.

In some embodiments of the present invention, the analytical data of the X-ray powder diffraction pattern of the crystal form C of the compound of formula (II) is shown in Table-3.

TABLE 3 analytical data of X-ray powder diffraction pattern
of crystal form C of compound of formula (II)

| NO. | 2-Theta | d(A) | BG | Height | I % | Area | I % | FWHM |
|---|---|---|---|---|---|---|---|---|
| 1 | 11.906 | 7.4269 | 199 | 621 | 17.7 | 8896 | 17.7 | 0.24 |
| 2 | 12.541 | 7.0526 | 235 | 857 | 24.4 | 7933 | 15.8 | 0.155 |
| 3 | 12.993 | 6.8078 | 229 | 580 | 16.5 | 4706 | 9.4 | 0.136 |
| 4 | 13.485 | 6.5606 | 226 | 762 | 21.7 | 7061 | 14.1 | 0.155 |
| 5 | 14.038 | 6.3036 | 201 | 1934 | 55.1 | 20010 | 39.9 | 0.173 |
| 6 | 16.285 | 5.4383 | 210 | 3511 | 100 | 50131 | 100 | 0.239 |
| 7 | 16.698 | 5.3048 | 230 | 1528 | 43.5 | 35932 | 71.7 | 0.394 |
| 8 | 17.45 | 5.078 | 254 | 770 | 21.9 | 9366 | 18.7 | 0.204 |
| 9 | 17.727 | 4.9993 | 252 | 1356 | 38.6 | 15329 | 30.6 | 0.189 |
| 10 | 18.181 | 4.8753 | 220 | 2657 | 75.7 | 30925 | 61.7 | 0.195 |
| 11 | 19.855 | 4.4679 | 219 | 595 | 16.9 | 6908 | 13.8 | 0.195 |
| 12 | 20.288 | 4.3735 | 188 | 2536 | 72.2 | 30866 | 61.6 | 0.204 |
| 13 | 20.701 | 4.2871 | 219 | 693 | 19.7 | 7201 | 14.4 | 0.174 |
| 14 | 22.399 | 3.9658 | 182 | 930 | 26.5 | 11059 | 22.1 | 0.199 |
| 15 | 23.405 | 3.7976 | 239 | 2075 | 59.1 | 34231 | 68.3 | 0.277 |
| 16 | 24.175 | 3.6784 | 276 | 834 | 23.8 | 9352 | 18.7 | 0.188 |
| 17 | 24.451 | 3.6375 | 252 | 759 | 21.6 | 9899 | 19.7 | 0.219 |
| 18 | 25.948 | 3.431 | 177 | 1167 | 33.2 | 24521 | 48.9 | 0.352 |
| 19 | 26.797 | 3.3241 | 183 | 477 | 13.6 | 5767 | 11.5 | 0.203 |
| 20 | 28.533 | 3.1257 | 171 | 530 | 15.1 | 6737 | 13.4 | 0.213 |
| 21 | 36.777 | 2.4418 | 207 | 622 | 17.7 | 6964 | 13.9 | 0.188 |

The present invention also provides a crystal form D of the compound of formula (III), wherein the X-ray powder diffraction pattern of the crystal form D has characteristic diffraction peaks at 2θ angles of 4.47±0.2°, 9.80±0.2°, 10.67±0.2°, 13.05±0.2°, 16.30±0.2°, 16.80±0.2°, 17.65±0.2°, 17.82±0.2°.

In some embodiments of the present invention, the analytical data of the X-ray powder diffraction pattern of the crystal form D of the compound of formula (III) is shown in Table-4.

TABLE 4 analytical data of X-ray powder diffraction pattern
of crystal form D of compound of formula (III)

| NO. | 2-Theta | d(A) | BG | Height | I % | Area | I % | FWHM |
|---|---|---|---|---|---|---|---|---|
| 1 | 4.473 | 19.7377 | 375 | 4844 | 100 | 45331 | 100 | 0.157 |
| 2 | 9.8 | 9.0181 | 176 | 1638 | 33.8 | 11819 | 26.1 | 0.121 |

TABLE 4-continued analytical data of X-ray powder diffraction pattern
of crystal form D of compound of formula (III)

| NO. | 2-Theta | d(A) | BG | Height | I % | Area | I % | FWHM |
|---|---|---|---|---|---|---|---|---|
| 3 | 10.666 | 8.2874 | 169 | 3717 | 76.7 | 30915 | 68.2 | 0.139 |
| 4 | 12.476 | 7.0888 | 184 | 1251 | 25.8 | 9047 | 20 | 0.121 |
| 5 | 13.051 | 6.778 | 177 | 1602 | 33.1 | 10873 | 24 | 0.114 |
| 6 | 13.427 | 6.589 | 166 | 1310 | 27 | 10573 | 23.3 | 0.135 |
| 7 | 16.13 | 5.4903 | 160 | 1106 | 22.8 | 37399 | 82.5 | 0.567 |
| 8 | 16.305 | 5.4318 | 160 | 2131 | 44 | 25688 | 56.7 | 0.202 |
| 9 | 16.799 | 5.2733 | 188 | 1641 | 33.9 | 15451 | 34.1 | 0.158 |
| 10 | 17.648 | 5.0213 | 181 | 2686 | 55.5 | 37888 | 83.6 | 0.236 |
| 11 | 17.82 | 4.9733 | 183 | 1431 | 29.5 | 43578 | 96.1 | 0.51 |
| 12 | 18.868 | 4.6993 | 175 | 646 | 13.3 | 7760 | 17.1 | 0.201 |
| 13 | 19.536 | 4.5402 | 208 | 533 | 11 | 4140 | 9.1 | 0.13 |
| 14 | 20.034 | 4.4284 | 167 | 740 | 15.3 | 12737 | 28.1 | 0.289 |
| 15 | 21.118 | 4.2035 | 165 | 712 | 14.7 | 6251 | 13.8 | 0.147 |
| 16 | 21.414 | 4.146 | 158 | 1336 | 27.6 | 12539 | 27.7 | 0.157 |
| 17 | 23.308 | 3.8132 | 225 | 1207 | 24.9 | 9801 | 21.6 | 0.136 |
| 18 | 24.271 | 3.6641 | 219 | 606 | 12.5 | 7376 | 16.3 | 0.204 |
| 19 | 25.91 | 3.4358 | 169 | 404 | 8.3 | 6287 | 13.9 | 0.261 |
| 20 | 27.31 | 3.2629 | 189 | 400 | 8.3 | 5345 | 11.8 | 0.224 |

The present invention also provides a crystal form E of the compound of formula (IV), wherein the X-ray powder diffraction pattern of the crystal form E has characteristic diffraction peaks at 2θ angles of 4.71±0.2°, 12.30±0.2°, 16.26±0.2°, 16.78±0.2°, 19.80±0.2°, 23.70±0.2°, 25.65±0.2°, 26.22±0.2°.

In some embodiments of the present invention, the analytical data of the X-ray powder diffraction pattern of the crystal form E of the compound of formula (IV) is shown in Table-5.

The present invention also provides a crystal form F of the compound of formula (IV), wherein the X-ray powder diffraction pattern of the crystal form F has characteristic diffraction peaks at 2θ angles of 5.79±0.2°, 9.75±0.2°, 14.03±0.2°, 15.67±0.2°, 17.46±0.2°, 18.86±0.2°, 20.42±0.2°, 20.99±0.2°.

In some embodiments of the present invention, the analytical data of the X-ray powder diffraction pattern of the crystal form F of the compound of formula (IV) is shown in Table-6.

TABLE 5 analytical data of X-ray powder diffraction pattern
of crystal form E of compound of formula (IV)

| NO. | 2-Theta | d(A) | BG | Height | I % | Area | I % | FWHM |
|---|---|---|---|---|---|---|---|---|
| 1 | 4.707 | 18.7589 | 309 | 3145 | 71.7 | 31611 | 82.2 | 0.168 |
| 2 | 11.631 | 7.6017 | 214 | 423 | 9.6 | 4278 | 11.1 | 0.17 |
| 3 | 12.302 | 7.1886 | 179 | 4388 | 100 | 38447 | 100 | 0.147 |
| 4 | 13.857 | 6.3854 | 163 | 337 | 7.7 | 3636 | 9.5 | 0.181 |
| 5 | 16.265 | 5.445 | 195 | 1333 | 30.4 | 23473 | 61.1 | 0.295 |
| 6 | 16.776 | 5.2802 | 224 | 2172 | 49.5 | 18674 | 48.6 | 0.144 |
| 7 | 17.547 | 5.05 | 229 | 1011 | 23 | 7789 | 20.3 | 0.129 |
| 8 | 18.02 | 4.9185 | 237 | 817 | 18.6 | 6923 | 18 | 0.142 |
| 9 | 18.554 | 4.7782 | 232 | 1272 | 29 | 16970 | 44.1 | 0.224 |
| 10 | 19.185 | 4.6225 | 221 | 473 | 10.8 | 5261 | 13.7 | 0.186 |
| 11 | 19.798 | 4.4807 | 205 | 2435 | 55.5 | 21568 | 56.1 | 0.148 |
| 12 | 21.257 | 4.1763 | 190 | 594 | 13.5 | 6130 | 15.9 | 0.173 |
| 13 | 21.726 | 4.0871 | 199 | 500 | 11.4 | 4069 | 10.6 | 0.136 |
| 14 | 22.854 | 3.888 | 166 | 721 | 16.4 | 11013 | 28.6 | 0.256 |
| 15 | 23.287 | 3.8166 | 181 | 891 | 20.3 | 14107 | 36.7 | 0.265 |
| 16 | 23.701 | 3.7509 | 230 | 1289 | 29.4 | 18099 | 47.1 | 0.235 |
| 17 | 24.626 | 3.612 | 203 | 552 | 12.6 | 7936 | 20.6 | 0.241 |
| 18 | 25.652 | 3.4699 | 211 | 1044 | 23.8 | 26708 | 69.5 | 0.429 |
| 19 | 26.223 | 3.3957 | 199 | 1116 | 25.4 | 17573 | 45.7 | 0.264 |
| 20 | 28.254 | 3.1559 | 191 | 491 | 11.2 | 11951 | 31.1 | 0.408 |
| 21 | 35.473 | 2.5285 | 141 | 225 | 5.1 | 3009 | 7.8 | 0.224 |
| 22 | 36.42 | 2.4649 | 122 | 312 | 7.1 | 4645 | 12.1 | 0.25 |

TABLE 6 analytical data of X-ray powder diffraction pattern
of crystal form F of compound of formula (IV)

| NO. | 2-Theta | d(A) | BG | Height | I % | Area | I % | FWHM |
|---|---|---|---|---|---|---|---|---|
| 1 | 5.786 | 15.2623 | 306 | 516 | 47.9 | 5073 | 28.7 | 0.165 |
| 2 | 7.426 | 11.8947 | 203 | 379 | 35.2 | 3988 | 22.6 | 0.176 |
| 3 | 8.703 | 10.1521 | 176 | 397 | 36.9 | 3247 | 18.4 | 0.137 |
| 4 | 9.75 | 9.0638 | 164 | 1016 | 94.3 | 9956 | 56.4 | 0.164 |
| 5 | 10.933 | 8.0861 | 170 | 338 | 31.4 | 2723 | 15.4 | 0.135 |
| 6 | 11.425 | 7.7387 | 177 | 354 | 32.9 | 3564 | 20.2 | 0.169 |
| 7 | 12.331 | 7.1718 | 163 | 481 | 44.7 | 4126 | 23.4 | 0.144 |
| 8 | 14.029 | 6.3074 | 151 | 735 | 68.2 | 7028 | 39.8 | 0.16 |
| 9 | 14.346 | 6.169 | 151 | 321 | 29.8 | 3591 | 20.3 | 0.188 |
| 10 | 15.666 | 5.652 | 156 | 760 | 70.6 | 9522 | 53.9 | 0.21 |
| 11 | 16.117 | 5.4947 | 162 | 322 | 29.9 | 4586 | 26 | 0.239 |
| 12 | 17.005 | 5.2098 | 182 | 192 | 17.8 | 2181 | 12.3 | 0.19 |
| 13 | 17.461 | 5.0748 | 203 | 706 | 65.6 | 6622 | 37.5 | 0.157 |
| 14 | 18.545 | 4.7804 | 207 | 363 | 33.7 | 6555 | 37.1 | 0.303 |
| 15 | 18.862 | 4.7007 | 204 | 1077 | 100 | 17667 | 100 | 0.275 |
| 16 | 19.705 | 4.5016 | 208 | 310 | 28.8 | 2593 | 14.7 | 0.14 |
| 17 | 20.419 | 4.3457 | 213 | 927 | 86.1 | 9467 | 53.6 | 0.171 |
| 18 | 20.991 | 4.2286 | 183 | 708 | 65.7 | 8791 | 49.8 | 0.208 |
| 19 | 22.767 | 3.9026 | 178 | 468 | 43.5 | 5533 | 31.3 | 0.198 |
| 20 | 23.337 | 3.8087 | 174 | 182 | 16.9 | 2200 | 12.5 | 0.203 |
| 21 | 24.048 | 3.6975 | 164 | 275 | 25.5 | 5361 | 30.3 | 0.327 |
| 22 | 25.411 | 3.5023 | 146 | 235 | 21.8 | 2471 | 14 | 0.176 |
| 23 | 27.184 | 3.2777 | 147 | 355 | 33 | 5433 | 30.8 | 0.257 |

The present invention also provides a crystal form G of the compound of formula (V), wherein the X-ray powder diffraction pattern of the crystal form G has characteristic diffraction peaks at 2θ angles of 4.59±0.2°, 12.24±0.2°, 15.93±0.2°, 16.66±0.2°, 18.46±0.2°, 19.72±0.2°, 22.10±0.2°, 23.56±0.2°.

In some embodiments of the present invention, the analytical data of the X-ray powder diffraction pattern of the crystal form G of the compound of formula (V) is shown in Table-7.

The present invention also provides a crystal form H of the compound of formula (V), wherein the X-ray powder diffraction pattern of the crystal form H has characteristic diffraction peaks at 2θ angles of 5.85±0.2°, 8.80±0.2°, 9.87±0.2°, 12.47±0.2°, 14.06±0.2°, 17.62±0.2°, 18.70±0.2°, 20.58±0.2°.

In some embodiments of the present invention, the analytical data of the X-ray powder diffraction pattern of the crystal form H of the compound of formula (V) is shown in Table-8.

TABLE 7 analytical data of X-ray powder diffraction pattern
of crystal form G of compound of formula (V)

| NO. | 2-Theta | d(A) | BG | Height | I % | Area | I % | FWHM |
|---|---|---|---|---|---|---|---|---|
| 1 | 4.59 | 19.2363 | 385 | 1667 | 38.4 | 15045 | 38.5 | 0.151 |
| 2 | 9.304 | 9.4971 | 191 | 598 | 13.8 | 5628 | 14.4 | 0.158 |
| 3 | 11.435 | 7.7317 | 235 | 684 | 15.7 | 4328 | 11.1 | 0.106 |
| 4 | 12.241 | 7.2246 | 202 | 4343 | 100 | 39033 | 100 | 0.151 |
| 5 | 15.929 | 5.5592 | 241 | 1991 | 45.8 | 21713 | 55.6 | 0.183 |
| 6 | 16.662 | 5.3164 | 306 | 838 | 19.3 | 5317 | 13.6 | 0.106 |
| 7 | 17.463 | 5.0742 | 251 | 484 | 11.1 | 3508 | 9 | 0.121 |
| 8 | 17.883 | 4.956 | 291 | 785 | 18.1 | 6452 | 16.5 | 0.138 |
| 9 | 18.455 | 4.8035 | 233 | 2706 | 62.3 | 32968 | 84.5 | 0.204 |
| 10 | 19.065 | 4.6513 | 240 | 267 | 6.1 | 2947 | 7.6 | 0.185 |
| 11 | 19.716 | 4.4991 | 260 | 804 | 18.5 | 7452 | 19.1 | 0.155 |
| 12 | 20.25 | 4.3817 | 248 | 324 | 7.5 | 4879 | 12.5 | 0.252 |
| 13 | 21.667 | 4.0982 | 251 | 304 | 7 | 1984 | 5.1 | 0.109 |
| 14 | 22.103 | 4.0183 | 237 | 923 | 21.3 | 6305 | 16.2 | 0.115 |
| 15 | 22.758 | 3.9042 | 254 | 570 | 13.1 | 6434 | 16.5 | 0.189 |
| 16 | 23.564 | 3.7724 | 230 | 1019 | 23.5 | 16018 | 41 | 0.263 |
| 17 | 24.587 | 3.6177 | 222 | 680 | 15.7 | 6927 | 17.7 | 0.171 |
| 18 | 25.378 | 3.5067 | 272 | 495 | 11.4 | 7444 | 19.1 | 0.252 |
| 19 | 25.868 | 3.4413 | 223 | 1128 | 26 | 17421 | 44.6 | 0.259 |
| 20 | 26.107 | 3.4105 | 234 | 408 | 9.4 | 10890 | 27.9 | 0.447 |
| 21 | 27.673 | 3.2209 | 211 | 116 | 2.7 | 2389 | 6.1 | 0.345 |
| 22 | 28.057 | 3.1776 | 213 | 433 | 10 | 6604 | 16.9 | 0.256 |
| 23 | 29.068 | 3.0694 | 189 | 288 | 6.6 | 4102 | 10.5 | 0.239 |
| 24 | 29.499 | 3.0255 | 176 | 140 | 3.2 | 3873 | 9.9 | 0.464 |

TABLE 8 analytical data of X-ray powder diffraction pattern
of crystal form H of compound of formula (V)

| NO. | 2-Theta | d(A) | BG | Height | I % | Area | I % | FWHM |
|---|---|---|---|---|---|---|---|---|
| 1 | 5.848 | 15.1009 | 258 | 680 | 70.3 | 7041 | 64.8 | 0.174 |
| 2 | 7.543 | 11.711 | 178 | 308 | 31.9 | 3618 | 33.3 | 0.197 |
| 3 | 8.803 | 10.0372 | 169 | 718 | 74.3 | 5934 | 54.6 | 0.139 |
| 4 | 9.869 | 8.9545 | 164 | 877 | 90.7 | 10726 | 98.8 | 0.205 |
| 5 | 10.968 | 8.0599 | 164 | 295 | 30.5 | 2465 | 22.7 | 0.14 |
| 6 | 11.688 | 7.5649 | 162 | 203 | 21 | 2735 | 25.2 | 0.226 |
| 7 | 12.471 | 7.0921 | 160 | 379 | 39.2 | 5453 | 50.2 | 0.241 |
| 8 | 13.144 | 6.73 | 156 | 286 | 29.6 | 2751 | 25.3 | 0.161 |
| 9 | 14.065 | 6.2915 | 146 | 337 | 34.9 | 2894 | 26.7 | 0.144 |
| 10 | 15.212 | 5.8196 | 161 | 284 | 29.4 | 2527 | 23.3 | 0.149 |
| 11 | 17.324 | 5.1146 | 144 | 132 | 13.7 | 3403 | 31.3 | 0.432 |
| 12 | 17.618 | 5.0298 | 150 | 967 | 100 | 10859 | 100 | 0.188 |
| 13 | 18.703 | 4.7404 | 161 | 396 | 41 | 8250 | 76 | 0.349 |
| 14 | 19.06 | 4.6524 | 159 | 336 | 34.7 | 5882 | 54.2 | 0.293 |
| 15 | 20.577 | 4.3128 | 169 | 381 | 39.4 | 7041 | 64.8 | 0.31 |
| 16 | 24.326 | 3.6559 | 129 | 142 | 14.7 | 1825 | 16.8 | 0.215 |

The present invention also provides a method for preparing the aforementioned crystal forms, including contacting a free base with an acid, washing, and drying.

The present invention also provides a pharmaceutical composition comprising a therapeutically effective amount of the compound described above or the crystal form(s) described above as an active ingredient and a pharmaceutically acceptable carrier.

The invention also provides a use of the compound described above in the manufacture of a medicament for the treatment of cerebral apoplexy or epilepsy.

The invention also provides a use of the crystal form described above in the preparation of a medicament for the treatment of cerebral apoplexy or epilepsy.

The invention also provides the use of the pharmaceutical composition described above in the preparation of a medicament for the treatment of cerebral apoplexy or epilepsy.

Technical Effect

The crystal form A and crystal form B of the compound of formula (I), the crystal form C of the compound of formula (II), the crystal form D of the compound of formula (III), the crystal form E and crystal form F of the compound of formula (IV), the crystal form G and crystal form H of the compound of formula (V) provided in the present invention have stable properties, good solubility, and good hygroscopicity. These crystal forms have good prospects in pharmaceutical development.

The preparation method of each crystal form of the present invention is simple; no harsh conditions and highly toxic solvents are required. The crystal forms obtained are of high purity and good yield; they are suitable for industrial scale-up.

Definition

Unless otherwise defined, the terms and phrases used herein have the meaning stated below. If a particular term or phrase is not specifically defined, such term or phrase should not be considered indefinite. Rather, terms are used within their accepted meanings. The trade names used herein are intended to refer to the corresponding commercial products or their active ingredients.

The compounds of the present invention can be prepared by various synthetic methods well-known to those skilled in the art, including the embodiments described below, embodiments combining the embodiments described below with other synthetic methods, and equivalent alternatives known to those skilled in the art. Preferred embodiments include but are not limited to those embodiments of the present invention.

Solvents used in the present invention are commercially available. The abbreviations used herein are as follows: aq is water; HATU is O-(7-Azabenzotriazol-1-yl)-N,N,N',N'-tetramethyluronium hexafluorophosphate; EDC is N-(3-Dimethylaminopropyl)-N'-ethylcarbodiimide; m-CPBA is 3-chloroperoxybenzoic acid; eq is equivalent; CDI is carbonyl diimidazole; DCM is dichloromethane; PE is petroleum ether; DIAD is diisopropyl azodicarboxylate; DMF is N,N-dimethylformamide; DMSO is dimethyl sulfoxide; EtOAc is ethyl acetate; EtOH is ethanol; MeOH is methanol; CBz is benzyloxycarbonyl, which is an amine protecting group; Boc is t-butylcarbonyl, which is an amine protecting group; HOAc is acetic acid; NaCNBH$_3$ is sodium cyanoborohydride; r.t. is room temperature; 0/N is overnight; THF is tetrahydrofuran; Boc$_2$O is di-tert-butyl dicarbonate; TFA is trifluoroacetic acid; DIPEA is diisopropylethylamine; SOCl$_2$ is thionyl chloride; CS$_2$ is carbon disulfide; TsOH is p-toluenesulfonic acid; NFSI is N-fluoro-N-(phenylsulfonyl) benzenesulfonamide; NCS is 1-chloropyrrolidine-2,5-dione; n-Bu$_4$NF is tetrabutylammonium fluoride; iPrOH is 2-propanol; mp is melting point; LDA is lithium diisopropylamide; CDCl$_3$ is deuterated chloroform; EA is ethyl acetate; MeOD is deuterated methanol; IPA is isopropanol; PDE is phosphodiesterase; AMP is adenosine monophosphate; GMP is guanosine monophosphate.

The solvents used in the present invention are commercially available. Commercially available compounds are described with catalog names provided by the suppliers.

The X-ray powder diffraction method is as follows:
Instrument: Bruker D8 ADVANCE X-ray diffractometer; target: Cu: K-Alpha; wavelength λ=1.54179 Å; tube voltage: 40 kV; tube current: 40 mA; scanning range: 4-40°; sample rotation speed: 15 rpm; scanning speed: 10°/min.

DETAILED DESCRIPTION OF THE
ILLUSTRATED EMBODIMENTS

The invention is described in detail below by the embodiments, but these embodiments are not intended to limit the invention. The present invention has been described in detail herein; the embodiments of the present invention are disclosed herein. It would be obvious for the person skilled in the art to make various modifications and changes to the embodiments of the present invention without departing from the spirit and scope of the invention.

Reference Embodiment 1—the Preparation of Compound 1

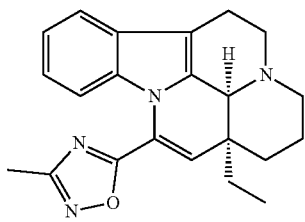

Compound 1

To a solution of (4¹S,13aS)-13a-ethyl-2,3,4¹,5,6,13a-hexahydro-1H-indolo[3,2,1-de]pyrido[3, 2,1-ij][1,5]naphthyridine-12-carboxylic acid (14 g, 43.4 mmol), 1-hydroxybenzotriazole (300 mg, 2.17 mmol) and triethylamine (31 mL, 217 mmol) in N,N-dimethylformamide (200 mL), O-(benzotriazol-1-yl)-N,N,N',N'-tetramethyluronium tetrafluoroborate (14.6 g, 45.6 mmol) and N-hydroxyacetamidine hydrochloride (5.28 g, 47.8 mmol) were added respectively, and the reaction mixture was stirred at room temperature overnight. Brine was added to the reaction mixture, then the mixture obtained was filtered, and the filtrate was diluted with water and extracted with dichloromethane. The extract was dried over anhydrous sodium sulfate, components of low boiling point were evaporated off. The remaining crude product in N,N-dimethylformamide was directly heated under microwave to 160° C. and reacted for 50 min. The crude product was purified by alkaline preparative High Performance Liquid Chromatography to obtain the target compound (4.0 g, yield: 25%).

$^1$H NMR (CDCl$_3$, 400 MHz) δ ppm 7.46 (d, J=6.8 Hz, 1H), 7.13-7.06 (m, 2H), 6.73 (d, J=8.0 Hz, 1H), 6.08 (s, 1H), 4.23 (s, 1H), 3.38-3.34 (m, 2H), 3.29-3.28 (m, 2H), 2.65-2.63 (m, 2H), 2.55-2.51 (m, 1H), 2.51 (s, 3H), 1.97-1.92 (m, 2H), 1.59-1.55 (m, 2H), 1.45-1.41 (m, 1H), 1.11-1.10 (m, 1H), 1.00 (t, J=7.2 Hz, 3H).

Embodiment 1—Preparation of the Compound of Formula (I) and Crystal Forms Thereof

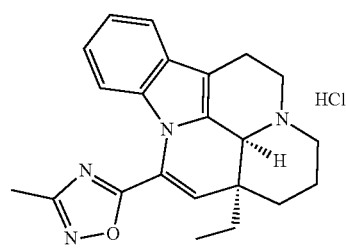

(I)

Preparation of the Compound of Formula (I)

Compound 1 (15.00 g, 41.61 mmol, 1.00 Eq.) was placed in a 500 mL three-neck flask. 150 mL of ethyl acetate and 15 mL of dichloromethane were added, the reaction system was replaced three times with nitrogen. 1N HCl/EA (60 mL) was added dropwise to the reaction liquid. The reaction mixture was stirred at 25° C. for 30 minutes, which led to the appearance of a large amount of white solid; the white solid was then filtrated. The filter cake was washed once with 50 mL of ethyl acetate. The filter cake was dried to give a white product (15.00 g, 37.79 mmol, 90.82%). $^1$H NMR (400 MHz, CDCl$_3$)=7.52 (dd, J=1.8 Hz, 1H), 7.24-7.22 (m, 2H), 6.78 (dd, J=4.0 Hz, 1H), 6.14 (s, 1H), 4.78 (s, 1H), 3.83-3.66 (m, 2H), 3.32-3.01 (m, 4H), 2.55 (s, 3H), 2.33-2.25 (m, 3H), 1.81-1.68 (m, 1H), 1.28-1.27 (m, 1H), 1.12 (t, J=8.0 Hz, 3H).

The Preparation of Crystal Form A:

Approximately 50 mg of the compound of formula (I) was added to methanol (1.5 mL). The suspension was stirred at 40° C. for three days. The remaining solid was centrifuged (10 min at 14,000 rpm) to separate and was dried overnight in a vacuum oven at 40° C. to give crystal form A.

The Preparation of Crystal Form B:

Crystal form B was prepared using the preparation method of crystal form A, except that methanol was replaced with acetone to obtain crystal form B.

Embodiment 2—Preparation of the Compound of Formula (II) and Crystal Form C Thereof

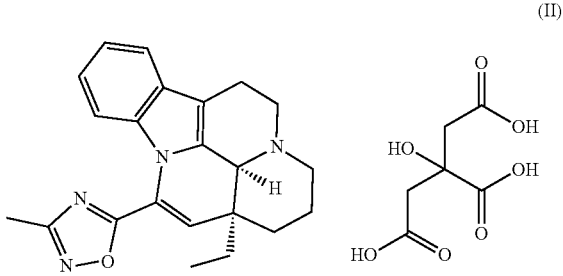

(II)

Compound 1 (2.00 g, 5.55 mmol, 1.00 eq) and citric acid (1.17 g, 6.11 mmol, 1.10 eq) were added to a 100 mL three-neck flask; 30 mL of ethanol was also added, and the reaction system was replaced three times with nitrogen. The reaction temperature was raised to 85-95° C. When the internal temperature reached 45-60° C., the reaction solution became clear. When the internal temperature reached 60° C. or above, turbidity began to appear. The reaction temperature was kept at 85-95° C. and the reaction mixture was stirred for 30 minutes, which lead to the appearance of a large amount of white solid. Heating was stopped and the internal temperature was lowered to 20-30° C., followed by filtering. The filter cake was washed once with 200 mL of ethanol. The filter cake was dried to give a white product (2.50 g, 4.56 mmol, 82.21%) which is crystal form C.

$^1$H NMR (400 MHz, MeOD) ppm 7.50-7.70 (m, 1H), 7.06-7.30 (m, 2H), 6.64-6.84 (m, 1H), 6.21 (s, 1H), 3.69-3.76 (m, 2H), 2.94-3.13 (m, 2H), 2.87 (dd, J=15.56, 1.00 Hz, 2H), 2.77 (d, J=15.31 Hz, 2H), 2.52 (s, 3H), 1.89-2.15 (m, 3H)), 1.11 (t, J=7.40 Hz, 3H).

Embodiment 3—Preparation of the Compound of Formula (III) and Crystal Form D Thereof

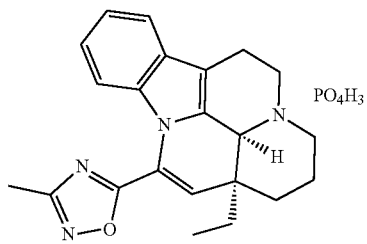

(III)

Preparation of the Compound of Formula (III):

Compound 1 (1.00 g, 2.77 mmol, 1.00 eq.) was placed in a 100 mL three-neck flask; 15 mL of ethanol was also added, and the reaction system was replaced three times with nitrogen. Phosphoric acid (319.36 mg, 2.77 mmol, 1.00 eq.) was added dropwise to the reaction liquid. The reaction temperature was raised to 60° C., the reaction mixture was kept at 60° C. and stirred for 30 minutes, which resulted in the appearance of a large amount of white solid. Heating was stopped; when the internal temperature was lowered to 20-30° C., the reaction mixture was filtered. The filter cake was washed once with 20 mL of ethanol. The filter cake was dried to give a white product (1.20 g, 2.61 mmol, 94.30%). $^1$H NMR (400 MHz, MeOD)=7.57 (d, J=6.8 Hz, 1H), 7.17 (t, J=6.0 Hz, 2H), 6.72 (d, J=7.5 Hz, 1H), 6.20 (s, 1H), 3.75 (d, J=6.3 Hz, 2H), 3.23 (d, J=15.1 Hz, 2H), 3.14-2.96 (m, 2H), 2.50 (s, 3H), 2.14-1.96 (m, 3H), 1.83-1.64 (m, 2H), 1.28-1.21 (m, 1H), 1.10 (t, J=7.3 Hz, 3H).

Preparation of Crystal Form D:

Approximately 30 mg of the compound of formula (III) was added to ethanol (0.5 mL) and was stirred at 40° C. for three days. The remaining compound was centrifuged (10 min at 14,000 rpm) to separate and was dried overnight in a vacuum oven at 40° C. to produce a dry solid, which is crystal form D.

Embodiment 4—Preparation of the Compound of Formula (IV) and Crystal Forms Thereof

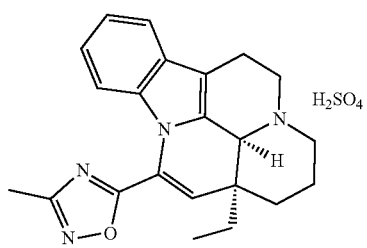

(IV)

Preparation of the Compound of Formula (IV):

Compound 1 (1.00 g, 2.77 mmol, 1.00 eq.) was added to a 100 mL three-neck flask, 15 mL of ethyl acetate and 3 mL of dichloromethane were also added; the reaction system was replaced three times with nitrogen. 1 mL of sulfuric acid (272.10 mg, 2.77 mmol, 1.00 eq.) diluted with water was added dropwise to the reaction liquid. The reaction temperature was kept at 25° C. and stirred for 30 minutes, which led to the appearance of a large amount of white solid. The white solid was filtered, the filter cake was washed once with 10 mL of ethyl acetate. The filter cake was dried to give a white product (1.10 g, 2.40 mmol, 86.61%). $^1$H NMR (400 MHz, MeOD)=7.65-7.53 (m, 1H), 7.25-7.12 (m, 2H), 6.79-6.68 (m, 1H), 6.19 (s, 1H), 5.02 (s, 1H), 3.90-3.74 (m, 2H), 3.34 (d, J=12.3 Hz, 1H), 3.26-3.04 (m, 3H), 2.48 (s, 3H), 2.06-1.89 (m, 3H), 1.81-1.67 (m, 2H), 1.29-1.16 (m, 1H), 1.10 (t, J=7.4 Hz, 3H).

Preparation of Crystal Form E:

About 30 mg of the compound of formula (IV) was added to the solvent IPA: H$_2$O=1:9 (0.5 mL) and stirred at 40° C. for three days. The residual compound was centrifuged (10 min at 14,000 rpm) to separate and was dried overnight in a vacuum oven at 40° C. to obtain a dry solid which is crystal form E.

Preparation of Crystal Form F:

Crystal form F was prepared using the preparation method for crystal form E, except that the solvent IPA:H$_2$O=1:9 was replaced with ethanol to obtain crystal form E.

Embodiment 5—Preparation of the Compound of Formula (V) and Crystal Forms Thereof

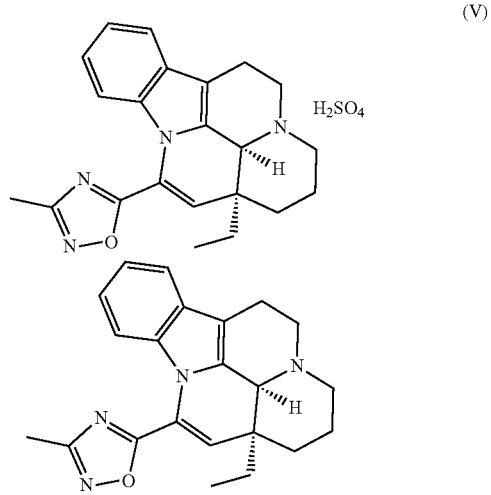

(V)

Preparation of the Compound of Formula (V):

Compound 1 (1.00 g, 2.77 mmol, 1.00 eq.) was added to a 100 mL three-neck flask, 15 mL of ethyl acetate and 3 mL of dichloromethane were also added; the reaction system was replaced three times with nitrogen. 1 mL of sulfuric acid (135.84 mg, 1.39 mmol, 0.50 eq.) diluted with water was added dropwise to the reaction liquid. The reaction temperature was kept at 25° C. and the reaction mixture was stirred for 30 minutes, which led to the appearance of a large amount of white solid. The white solid was filtered; the filter cake was washed once with 10 mL of ethyl acetate. The filter cake was dried to give a white product (500.00 mg, 1.09 mmol, 39.37%). $^1$H NMR (400 MHz, MeOD)=7.59 (dd, J=2.4, 4.6 Hz, 1H), 7.27-7.08 (m, 2H), 6.73 (d, J=7.5 Hz, 1H), 6.29-6.13 (m, 1H), 5.06 (d, J=14.8 Hz, 1H), 3.93-3.73 (m, 2H), 3.47-3.31 (m, 1H), 3.28-3.02 (m, 3H), 2.53-2.41 (m, 3H), 2.11-1.88 (m, 3H), 1.77 (d, J=4.8 Hz, 2H), 1.25 (d, J=10.3 Hz, 1H), 1.15-1.02 (m, 3H).

Preparation of Crystal Form G:

Approximately 30 mg of the compound of formula (V) was added to a solvent (0.5 mL). The reaction mixture was stirred at 40° C. for three days. Centrifugation (10 min at 14,000 rpm) was performed to separate the residual solid compound; the separated compound was dried under vacuum at 40° C. overnight. A dry solid is obtained which is crystal form G.

Preparation of Crystal Form H:

Crystal form H was prepared using the preparation method of crystal form G, except that the solvent IPA: $H_2O$=1:9 was replaced with EtOAc to obtain crystal form H.

Experimental Example 1: The In Vitro Detection of Phosphodiesterase (PDE)

Principle of the Experiment:

The assay measures PDE1A enzyme activity based on fluorescence polarization detection of AMP/GMP production. The principle of the reaction is to replace the binding of AMP/GMP to its antibody by AlexaFluor 633 labeled AMP/GMP.

Experimental Reagents:

Reaction buffer: 10 mM Tris-HCl, pH=7.5, 5 mM magnesium chloride, 0.01% Brij 35, 1 mM DTT, and 1% DMSO;

Enzyme substrate: 1M cAMP or cGMP ($Ca^{2+}$-calmodulin as a cofactor of PDE1A);

Detection Reagents:

Transcreener® AMP2/GMP2 antibody;

AMP2/GMP2 AlexaFluor 633 marker.

Experimental Procedures and Methods:

1. Human enzyme to be tested (purchased from Signal-Chem) and the substrate were diluted with a freshly prepared reaction buffer.

2. An enzyme solution (concentration: 3 pM) was added to the wells of a reaction plate.

3. Echo 550 was employed to add a number of 100% DMSO compound solutions to the wells of the reaction plate at required concentrations; said wells of the reaction plate contain the enzyme solution. The reaction plate was then incubated at room temperature for 10 minutes.

4. The substrate solution was added to the wells of the reaction plate containing the enzyme and the compound solution to initiate the reaction.

5. The reaction plate was incubated for 1 hour at room temperature with shaking.

6. A detection mixture (a stop buffer in the tracer and the antibody) was added to stop the enzymatic reaction; the reaction plate was incubated for 90 minutes with shaking.

7. The following devices were used for detection: EnVision (PerkinElmer), Cy5FP Ex FP 620, Em S-pol 688/P-pol 688, FP mirror D658fp/D688; fluorescence polarization was detected using Ex/Em 620/688.

Data Analysis:

Enzymatic activity corresponding to the FP signal was retrieved in an AMP/GMP standard curve using DMSO as a control in an Excel table. The enzymatic activity was converted to nM product concentration. An analysis was performed using GraphPad Prism and $IC_{50}$ values were calculated.

The experimental results are shown in Table 1:

TABLE 1

| $IC_{50}$ values measured by PDE1 detection | |
|---|---|
| Tested compound | PDE1 |
| Compound 1 | 1 uM < B ≤ 20 uM |

What is claimed is:

1. A crystal form A of a compound of formula (I)

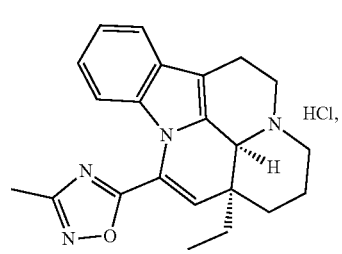

(I)

wherein an X-ray powder diffraction pattern of the crystal form A has characteristic diffraction peaks at 2θ angles of 9.14±0.2°, 10.43±0.2°, 11.38±0.2°, 12.54±0.2°, 13.86±0.2°, 19.04±0.2°, 19.36±0.2°, 21.00±0.2°.

2. The crystal form A of the compound of formula (I) according to claim 1, wherein analytical data of the X-ray powder diffraction pattern thereof is shown in Table 1.

3. A crystal form B of a compound of formula (I)

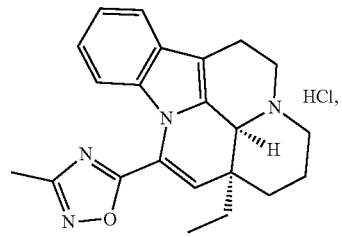

(I)

wherein an X-ray powder diffraction pattern of the crystal form B has characteristic diffraction peaks at 2θ angles of 9.17±0.2°, 11.75±0.2°, 12.16±0.2°, 12.67±0.2°, 15.14±0.2°, 17.81±0.2°, 20.54±0.2°, 22.34±0.2°.

4. The crystal form B of the compound of formula (I) according to claim 3, wherein analytical data of the X-ray powder diffraction pattern thereof is shown in Table-2.

5. A crystal form C of a compound of formula (II)

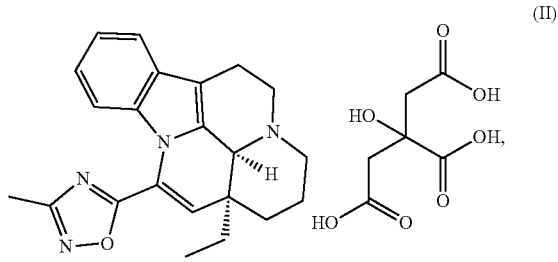

(II)

wherein an X-ray powder diffraction pattern of the crystal form C has characteristic diffraction peaks at 2θ angles of 14.04±0.2°, 16.28±0.2°, 16.70±0.2°, 17.73±0.2°, 18.18±0.2°, 20.29±0.2°, 23.40±0.2°, 25.95±0.2°.

6. The crystal form C of the compound of formula (II) according to claim 5, wherein analytical data of the X-ray powder diffraction pattern thereof is shown in Table-3.

7. A crystal form D of a compound of formula (III)

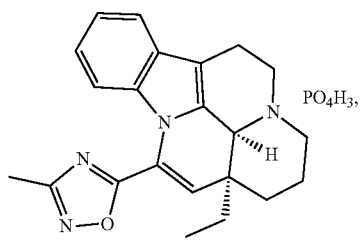

(III)

wherein an X-ray powder diffraction pattern of the crystal form D has characteristic diffraction peaks at 2θ angles of 4.47±0.2°, 9.80±0.2°, 10.67±0.2°, 13.05±0.2°, 16.30±0.2°, 16.80±0.2°, 17.65±0.2°, 17.82±0.2°.

8. The crystal form D of the compound of formula (III) according to claim 7, wherein analytical data of the X-ray powder diffraction pattern thereof is shown in Table-4.

9. A crystal form E of a compound of formula (IV)

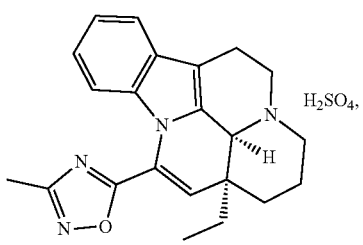

(IV)

wherein an X-ray powder diffraction pattern of the crystal form E has characteristic diffraction peaks at 2θ angles of 4.71±0.2°, 12.30±0.2°, 16.26±0.2°, 16.78±0.2°, 19.80±0.2°, 23.70±0.2°, 25.65±0.2°, 26.22±0.2°.

10. The crystal form E of the compound of formula (IV) according to claim 9, wherein analytical data of the X-ray powder diffraction pattern thereof is shown in Table-5.

11. A crystal form F of a compound of formula (IV)

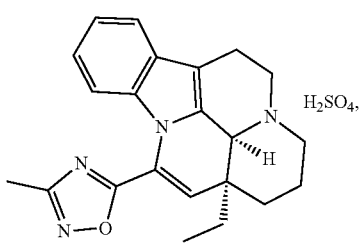

(IV)

wherein an X-ray powder diffraction pattern of the crystal form F has characteristic diffraction peaks at 2θ angles of 5.79±0.2°, 9.75±0.2°, 14.03±0.2°, 15.67±0.2°, 17.46±0.2°, 18.86±0.2°, 20.42±0.2°, 20.99±0.2°.

12. The crystal form F of the compound of formula (IV) according to claim 11, wherein analytical data of the X-ray powder diffraction pattern thereof is shown in Table-6.

13. A crystal form G of a compound of formula (V)

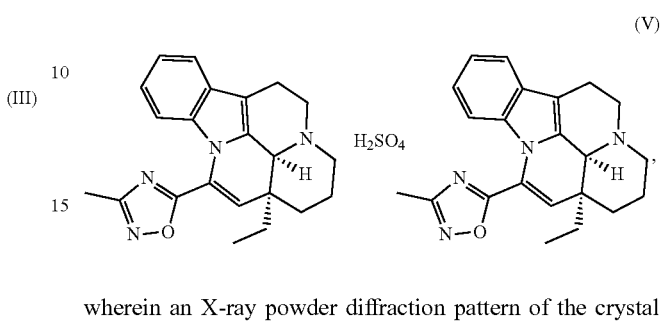

(V)

wherein an X-ray powder diffraction pattern of the crystal form G has characteristic diffraction peaks at 2θ angles of 4.59±0.2°, 12.24±0.2°, 15.93±0.2°, 16.66±0.2°, 18.46±0.2°, 19.72±0.2°, 22.10±0.2°, 23.56±0.2°.

14. The crystal form G of the compound of formula (V) according to claim 13, wherein analytical data of the X-ray powder diffraction pattern thereof is shown in Table-7.

15. A crystal form H of a compound of formula (V)

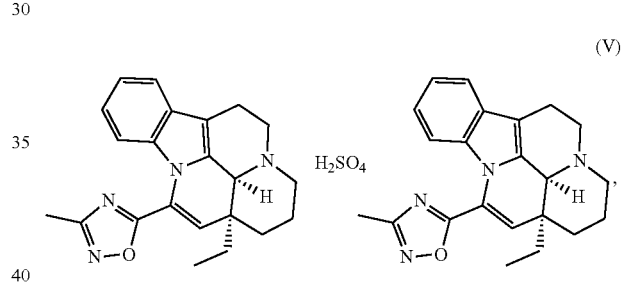

(V)

wherein an X-ray powder diffraction pattern of the crystal form H has characteristic diffraction peaks at 2θ angles of 5.85±0.2°, 8.80±0.2°, 9.87±0.2°, 12.47±0.2°, 14.06±0.2°, 17.62±0.2°, 18.70±0.2°, 20.58±0.2°.

16. The crystal form H of the compound of formula (V) according to claim 15, wherein analytical data of the X-ray powder diffraction pattern thereof is shown in Table-8.

17. A method for preparing the crystal form according to claim 1, comprising contacting the free base of compound 1:

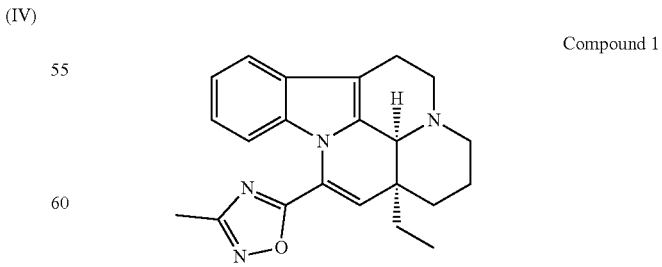

Compound 1 with HCl, washing, and drying.

18. A method for preparing the crystal form according to claim 2, comprising contacting the free base of compound 1:

Compound 1
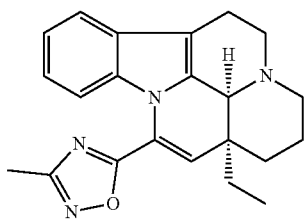

with HCl, washing, and drying.

19. A method for preparing the crystal form according to claim 3, comprising contacting the free base of compound 1:

Compound 1
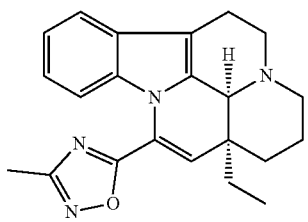

with HCl washing, and drying.

20. A method for preparing the crystal form according to claim 4, comprising contacting the free base of compound 1:

Compound 1
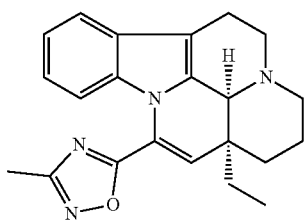

with HCl washing, and drying.

21. A method for preparing the crystal form according to claim 5, comprising contacting the free base of compound 1:

Compound 1
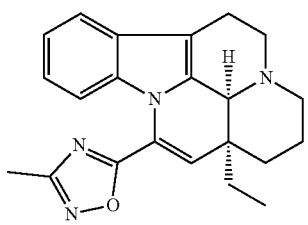

with citric acid, washing, and drying.

22. A method for preparing the crystal form according to claim 6, comprising contacting the free base of compound 1:

Compound 1
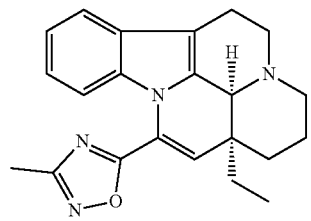

with citric acid, washing, and drying.

23. A method for preparing the crystal form according to claim 7, comprising contacting the free base of compound 1:

Compound 1
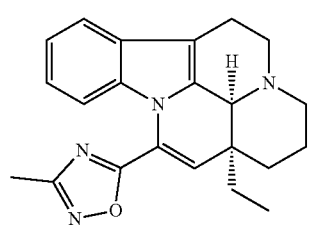

with phosphoric acid, washing, and drying.

24. A method for preparing the crystal form according to claim 8, comprising contacting the free base of compound 1:

Compound 1
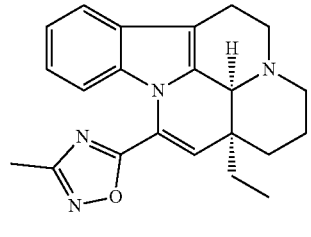

with phosphoric acid, washing, and drying.

25. A method for preparing the crystal form according to claim 9, comprising contacting the free base of compound 1:

Compound 1
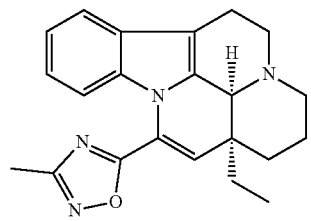

with sulfuric acid, washing, and drying.

26. A method for preparing the crystal form according to claim 10, comprising contacting the free base of compound 1:

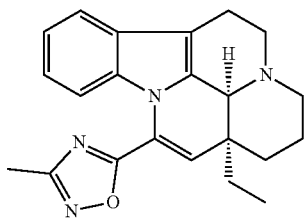
Compound 1 with sulfuric acid, washing, and drying.

27. A method for preparing the crystal form according to claim 11, comprising contacting the free base of compound 1:

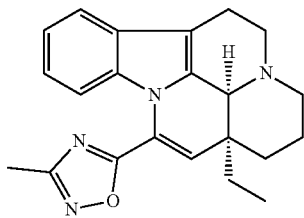
Compound 1 with sulfuric acid, washing, and drying.

28. A method for preparing the crystal form according to claim 12, comprising contacting the free base of compound 1:

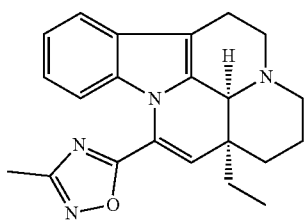
Compound 1 with sulfuric acid, washing, and drying.

29. A method for preparing the crystal form according to claim 13, comprising contacting the free base of compound 1:

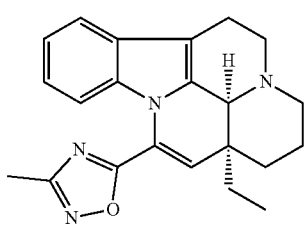
Compound 1 with sulfuric acid, washing, and drying.

30. A method for preparing the crystal form according to claim 14, comprising contacting the free base of compound 1:

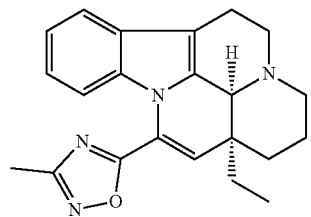
Compound 1 with sulfuric acid, washing, and drying.

31. A method for preparing the crystal form according to claim 15, comprising contacting the free base of compound 1:

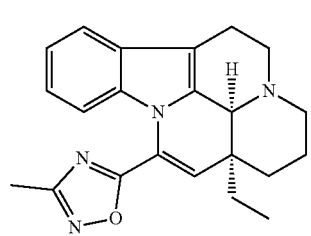
Compound 1 with sulfuric acid, washing, and drying.

32. A method for preparing the crystal form according to claim 16, comprising contacting the free base of compound 1:

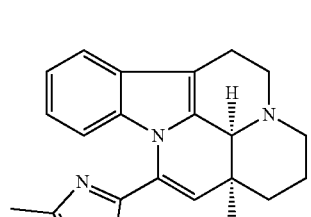
Compound 1 with sulfuric acid, washing, and drying.

33. A method for treating cerebral apoplexy or epilepsy in a subject, comprising administering the crystal form according to claim 1 to the subject.

34. A method for treating cerebral apoplexy or epilepsy in a subject, comprising administering the crystal form according to claim 2 to the subject.

35. A method for treating cerebral apoplexy or epilepsy in a subject, comprising administering the crystal form according to claim 3 to the subject.

36. A method for treating cerebral apoplexy or epilepsy in a subject, comprising administering the crystal form according to claim 4 to the subject.

37. A method for treating cerebral apoplexy or epilepsy in a subject, comprising administering the crystal form according to claim 5 to the subject.

* * * * *